United States Patent [19]

Gutierrez et al.

[11] 3,985,808

[45] Oct. 12, 1976

[54] PROCESS FOR THE PREPARATION OF SELECTIVELY HALOGENATED KETONES AND KETALS

[75] Inventors: Eddie N. Gutierrez, Fort Lee; Robert C. Reardon, Jr., Tenafly, both of N.J.

[73] Assignee: Lever Brothers Company, New York, N.Y.

[22] Filed: Oct. 30, 1975

[21] Appl. No.: 627,162

Related U.S. Application Data

[62] Division of Ser. No. 426,771, Dec. 20, 1973, Pat. No. 3,944,568.

[52] U.S. Cl. .............................. 260/586 R; 260/338; 260/340.6; 260/340.7; 260/340.9; 260/590 C; 260/591; 260/592; 260/593 H; 260/611 R; 260/612 R; 260/612 D; 260/615 A
[51] Int. Cl.[2] ................... C07C 41/10; C07C 45/00
[58] Field of Search ............. 260/338, 340.6, 340.7, 260/340.9, 586 R, 590 C, 591, 592, 593 H, 611 R, 612 R, 612 D, 615 A

[56] References Cited

UNITED STATES PATENTS

| 3,453,290 | 7/1969 | Propper | 260/340.9 |
| 3,824,292 | 7/1974 | Kirby | 260/615 A |

OTHER PUBLICATIONS

"The Chem. of the Carbonyl Group," Patai, Editor, pp. 188–191, 207–210, (1966), John Wiley and Sons.

Primary Examiner—Norman Morgenstern
Attorney, Agent, or Firm—James J. Farrell; Kenneth F. Dusyn; Melvin H. Kurtz

[57] ABSTRACT

A method is disclosed wherein selectively halogenated ketals, and ultimately, halogenated ketones are prepared by treating secondary alcohols or halohydrins with halogen in an organic solvent under conditions of ordinary temperature and pressure. This method obviates the need for extreme times, temperatures and complex equipment while resulting in higher yields than obtained heretofore.

11 Claims, No Drawings

PROCESS FOR THE PREPARATION OF SELECTIVELY HALOGENATED KETONES AND KETALS

This is a division of application Ser. No. 426,771, filed Dec. 20, 1973 now U.S. Pat. No. 3,944,568.

BACKGROUND OF THE INVENTION

1. Field of the Invention

This invention pertains to a new and improved method for the preparation of selectively halogenated ketals and ketones from secondary alcohols or halohydrins, more specifically, selectively chlorinated or brominated ketals and ketones.

2. Description Of The Prior Art

Heretofore, it has been extremely difficult to obtain selectively and symmetrically dihalogenated ketones and ketals, Oxidation of chlorohydrin (1-chloro-2-propanol) to chloroacetone has been reported in the literature to occur by any of the following reactions:

a. $K_2Cr_2O_7 + H_2SO_4$
b. $HNO_3$
c. HOCl — Markownikoff Ann. 153, 254–255 (1870)
d. $Ca(OCl)_2$ — Suknewitsch, Tschilingarjan Ber. 69, 1539 (1936).

None of the aforementioned references disclose or suggest oxidations by $Cl_2$ or $Br_2$. Farkas et al in J. Am. Chem. Soc. 71, 2827 et seq., disclose the oxidation of alcohols by bromine in the presence of bromate ion. The object, however, of the Farkas et al disclosure is to avoid substitution. Furthermore, there is no disclosure in Farkas et al relative to selective and symmetrical dihalogenation. Additionally, prior art chlorinations and brominations yielded mixtures of halogenated ketones which were difficult to separate. The separation of isomers aspect of this invention is considered to be an additional novel feature of the instant application.

DESCRIPTION OF THE INVENTION

This invention relates to a novel method for the preparation of selectively and symmetrically halogenated, more specifically, selectively chlorinated or brominated ketals and ketones. The instant process differs from processes known heretofore in that the reaction takes place in a solvent selected from monohydric and polyhydric alcohols at conditions of ordinary temperature and pressure.

The methods for preparing these halogenated derivatives may be illustrated as follows:

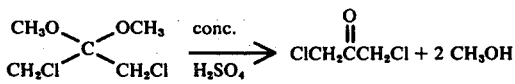

Succinctly stated, the method of the instant invention simultaneously accomplishes an oxidation, halogenation and acetylation in one process.

Although chlorination of secondary alcohols and chlorohydrins have been illustrated, the reactants may be brominated in the same manner. It is to be understood that a bromohydrin would be the starting material when a 1-halogenated-2-propanol is contemplated.

Accordingly, it is an object of this invention to provide a method of preparing selectively halogenated ketals which comprises treating with a halogen selected from the group consisting of chlorine and bromine compounds of the formula:

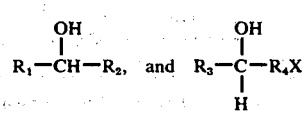

wherein $R_1$, $R_2$, $R_3$, and $R_4$ may be a straight chain alkyl group of from 1 20 carbon atoms, an alkylaryl group wherein the alkyl moiety is a straight chain of from 1 to 20 carbon atoms, a branched chain alkyl group of from 3 to 20 carbon atoms, and phenyl, provided that when either of the pair of $R_1$, $R_2$, and $R_3$, and $R_4$ are phenyl or a branched chain, the other member of the pair is alkyl as previously defined, or $R_1$ and $R_2$ or $R_3$ and $R_4$ may further be taken together to form a cycloalkyl ring having at least 6 carbon atoms, and wherein X is chlorine or bromine, said treatment being in an organic solvent selected from the group consisting of monohydric and polyhydric alcohols wherein the ratio of said solvent to secondary alcohol or halohydrin is from about 5:1 to about 20:1 and at a temperature of from about 0°C to about 80°C. Starting materials having mixed structures, i.e., straight and branched chain alkyl groups (as defined above) on the same carbinol are within the scope of this disclosure.

It is a further object of the invention to obtain in high yields selectively and symmetrically dihalogenated ketones and ketals wherein the symmetrically dihalogenated products are easily separable from other isomeric reaction products.

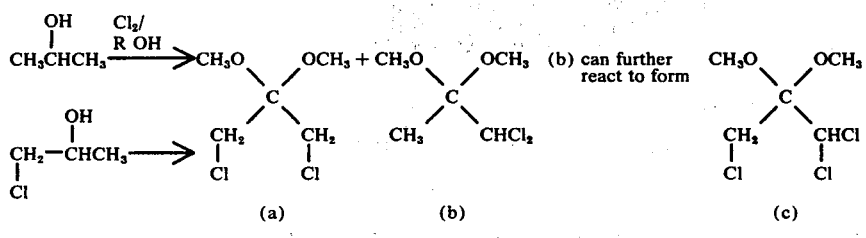

(R will be more fully described hereunder) Separation of (a) and (b) or (c) can be accomplished easily.

The symmetrically halogenated products, (c), may be hydrolyzed under acidic conditions to produce halogenated ketones. For example:

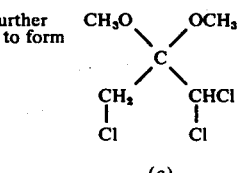

It is also an object of this invention to provide a more economical and feasible method for the preparation of compounds which find use as fungicides, treating agents useful in the fiber industry, resinification agents in the formation of resinous aromatic hydrocarbons, pesticides and plasticizers.

The novel process of the instant invention may be exemplified as follows:

(a) Chlorination of secondary alcohols

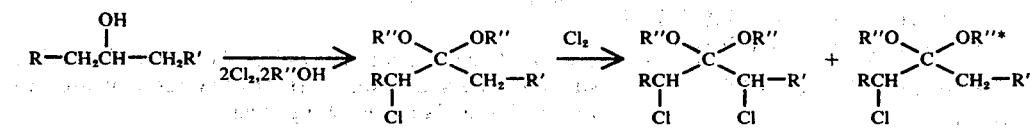

(b) Chlorination of chlorohydrins

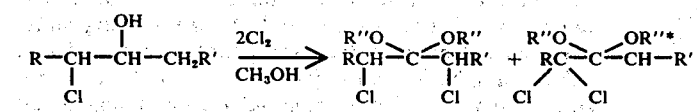

The symmetrically chlorinated products of either (a) or (b) may be hydrolyzed under acidic conditions to produce chlorinated ketones. For example:

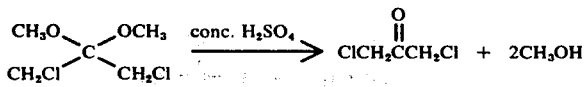

*The unsymmetrical reaction products may be further halogenated, whereas no further halogenation occurs with the symmetrical reaction products.
NOTE:
Bromination of the secondary alcohols or halohydrins would proceed in the same manner with similar results. Two moles of halogen are required to insure the initial oxidation of the carbinol (—COH) to ketone.

As aforestated, this method affects an oxidation, halogenation and acetylation in one process. What has been illustrated above are the two general routes, according to the instant invention for the formation of selectively and symmetrically dichlorinated ketones and ketals. Although chlorine has been illustrated, bromine may also be used with similar results.

One of the stated objects of the invention is the fact that a symmetrical dihalogenated product is easily separable from the isomeric reaction products. As aforestated, the symmetrically formed dichloro ketal differs from the unsymmetrically formed products in that chlorination stops at the symmetrical stage while the unsymmetrical, e.g.

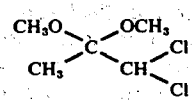

can be chlorinated further to yield, e.g.

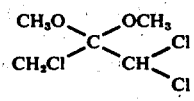

The separation of the symmetrical product from the unsymmetrical product is generally accomplished by crystallization at −70°C.

The major advantage of this method over prior art is that the latter discloses no means of producing dichlorinated ketals from secondary alcohols in a one-step process. The oxidation occurs under anhydrous conditions, and it is believed that the methyl hypochlorite formed is acting as an oxidizing agent producing ketone and hydrogen chloride, which is the catalyst for ketal formation. For example,

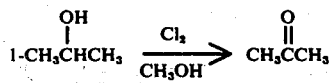

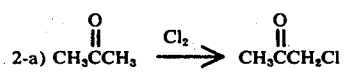

both steps are occurring

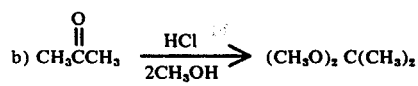

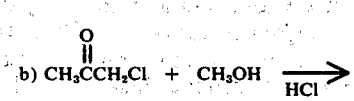

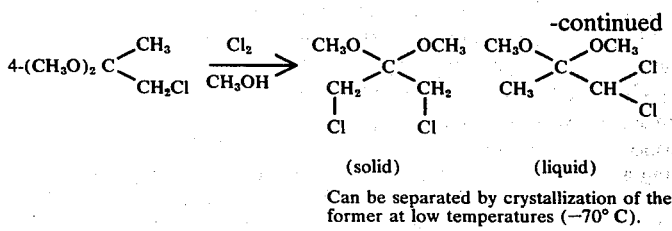

(solid) (liquid)

Can be separated by crystallization of the former at low temperatures (−70° C).

The initial oxidation produces its own catalyst so that reactions 2b and 3b can occur in the same reaction vessel.

The method of the present invention is conveniently carried out by slowly bubbling halogen gas through an alcoholic solution of the secondary alcohol or halohydrin at room temperature and atmospheric pressure. The method requires no special apparatus. All that is required is control of the halogen gas being introduced and stirring. Reactions for the secondary alcohols are typically short in duration, give products of high purity, produce no undesirable products of decomposition and are nearly quantitative based on molecular halogen.

Previously mentioned was the selective and symmetrical aspect of the instant invention. The process is selective in that only atoms that are alpha to the carbinol (—COH) group are halogenated. Another surprising feature is that when a straight chain carbinol is treated according to the process of this invention the selectivity persists regardless of the chain length. Additionally, the selectivity will persist where the carbinol being treated is one having a mixed structure, i.e. a straight chain portion and another portion comprising either a branched chain or some type of ring structure. The halogenation will take place predominately on the straight chain portion of the compound and substitute at the carbon alpha to the carbinol group.

It is our belief, although not intending to be bound by such, that both the selectivity and degree of halogenation obtained by the instant invention are due to steric hindrance. Steric hindrance, of course, is the nonoccurrence of an expected chemical reaction, due to inhibition by a particular atomic grouping. The steric hindrance is present, initially, in the ketal itself by virtue of the alkoxy groups present in the compound. This steric hindrance causes the reaction to take place at the alkyl portion of the molecule. The second role played by steric hindrance relates to the degree of halogenation. Where the starting carbinol is a straight chain compound, the product obtained by the instant process is predominately a symmetrically dihalogenated ketal. When the starting material is of mixed structure the resultant product can be a monohalogenated or polyhalogenated ketal. In both instances, the products are selectively halogenated and also can be acid hydrolyzed to the respective halogenated ketones.

When the first halogen substitution takes place, the ketal that is formed in the initial stages of the reaction, a sterically hindered moiety results, e.g.

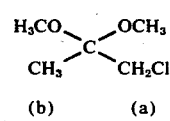

(b)      (a)

By virtue of such steric hinderance the next halogen substitution will occur primarily at (b).

As a matter of fact, what is believed to be occurring simultaneously are the following reactions:

(1) Chlorination of secondary alcohols

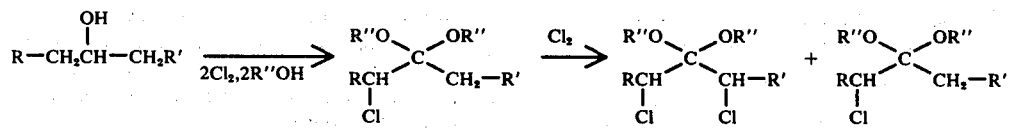

(2) Chlorination of chlorohydrins

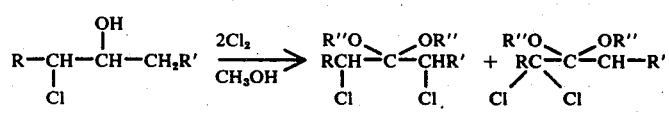

As aforestated, it is believed that hydrohalogen acid, viz., HCl or HBr, a known catalyst for ketal formation, is produced in the halogenation step. Stated otherwise, the initial halogenation step produces its own catalyst for the production of the monohalogenated ketal that ultimately results in high yields of symmetrically dihalogenated ketals. It is also reasonable to conclude that in view of the condiderable amount of alcohol used, stable hypohalites as well as the hydrohalogen are also formed, which are contributing to the initial halogenation as the primary halogenating agent.

Typical secondary alcohols that may be used cover a broad spectrum. They are selected from compounds of the formula:

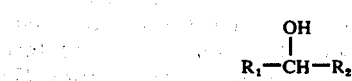

wherein $R_1$ and $R_2$ may be straight chain alkyl groups of from 1 to 20 carbon atoms such as isopropanol, 2-butanol, 2-pentanol, 3-pentanol, 2-hexanol, 3-hexanol and the like.

$R_1$ and $R_2$ may also be selected from alkylaryl groups wherein the alkyl moiety may be a straight chain of from 1 to 20 carbon atoms exemplified by compounds such as secondary phenethyl alcohol, 1-phenyl-2-propanol and the like. It has been found that when $R_1$ is phenyl, for example α-methylbenzyl alcohol, a monochloro-1,3-dioxolone derivative is formed when using a halogen/ethylene glycol system. The result is a monohalogenated product which is resistant to further chlorination because of the extreme steric hindrances of the phenyl and dioxolane groups. The reaction is exemplified as follows:

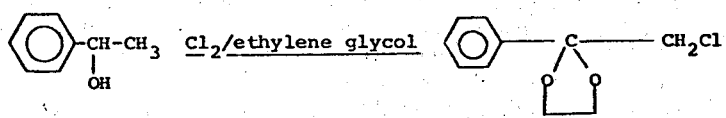

$R_1$ and $R_2$ may further be taken together to form a cycloalkyl ring having at least 6 carbon atoms. Exemplary compounds of this category are illustrated by the following: cyclohexanol, cycloheptanol, cyclooctanol, cyclononanol, cyclodecanol and the like.

$R_1$ and $R_2$ may be a branched chain alkyl group of from 3 to 20 carbon atoms provided that when either of $R_1$ or $R_2$ is a branched chain the other member is a straight chain alkyl group as previously defined. Examples of these compounds are: 3-methyl-2-butanol, 3-methyl-2-pentanol, 4-methyl-2-butanol, 4,4-dimethyl-2-pentanol, methyl isopropyl carbinol, methyl-t-butyl carbinol and the like.

Typical halohydrins that may be used in the process of the instant invention are selected from the compounds having the formula:

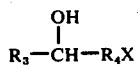

wherein $R_3$ and $R_4$ are the same as $R_1$ and $R_2$ which have been previously defined. X may be either chlorine or bromine. In all instances, however, X will be alpha to the carbinol. Compounds falling into this category are chlorohydrin, bromohydrin, 3-chloro-2-pentanol, 3-bromo-2-pentanol, 3-chloro-2-hexanol, 3-bromo-2-heptanol, 1-phenyl-3-chloro-2-propanol, 1-phenyl-3-bromo-2-propanol, 2-chloro-1-cyclohexanol, 2-bromo-1-cyclohexanol, 3-methyl-3-chloro-2-butanol, 4,4-dimethyl-3-chloro-2-pentanol, 4,4-dimethyl-3-bromo-2-pentanol, 3,3-dimethyl-1-chloro-2-butanol, 3,3-dimethyl-1-bromo-2-butanol.

The solvent media may be selected from mono and polyhydric alcohols. While we do not wish to be bound by any particular mechanism, it is our view that the use of methanol or any alcohol containing only C-H groups to which the -OH groups are attached prevents the ketal from decomposing into a ketone and the respective alcohol. It appears that the use of the above-mentioned type of alcohols shifts the equilibrium to the right. This prevention of decomposition of ketal is accomplished by insuring that there is an excess of the alchohol as compared to the ketal, said ratio being from about 5:1 to about 20:1, preferably about 10:1, most preferably about 5:1 in favor of the alcohol. The use of an excess of alcohol also insures the obtention of predominately selectively and symmetrically dihalogenated product. While any mono and polyhydric alcohols having 1–5 carbons are generally usable in the instant invention, most preferred are those wherein the number of hydroxyl groups is equal to the number of carbon atoms and each atom is hydroxylated. Alcohols falling into this category are alcohols such as methanol, ethylene glycol, gylcerol, sorbitol. Alcohols higher than glycerol are generally solids, therefore it will be necessary that heat be applied to initiate the reaction.

Alcohols such as ethanol and 2,3-butanediol are within the scope of this invention, however, some oxidation of the alcohol will occur. Tolerable amounts of alcohol oxidation can readily be determined by utilizing the instant process. However, clean reactions, i.e., no alcohol oxidation, are obtained when the preferred alcohols are used.

The preferred alcohols are believed to form hypohalides which participate in the initial halogenation by providing either chloronium or bromonium ions. In addition, it has been found that at the end of the reaction the starting alcohol is reformed from its hypohalite. This reformation is believed to occur either during or as a result of the halogenation step.

Although the invention is preferably carried out at ordinary conditions of temperature and pressure, a wide range of temperatures and pressures is contemplated, i.e., from about 0°C to about 80°C, preferably from about 20°C to about 40°C and most preferably from about 25°C to about 30°C and from about 1 to about 10 atmospheres of pressure. The solvents, as previously stated, may be selected from mono or polyhydric alchohls. Elsewhere in the specification the criticality of the alcohol solvents has been discussed. The proportion of chlorine and bromine used will depend upon the degree of halogenation desired, however a molar ratio of about 2:1 to about 5:1 of halogen to secondary alcohol or halohydrin is preferred. The reaction should be carried out with moderate stirring accompanied by a slow introduction of halogen in order to avoid possible explosions that may be caused by high concentrations of hypohalite resulting from incomplete reactions of same with secondary alcohol or halohydrin.

The acids used to accomplish the hydrolysis of the halogenated ketals to the halogenated ketones can be any of the conventional mineral acids such as hydrochloric, sulfuric, phosphoric, chloric, chlorous, hydrobromic, hydrofluoric, sulfurous, di and trifluoroacetic. Generally, any acid containing an electron withdrawing group may be used. The acid conditions contemplated herein are strong acid conditions, i.e., undiluted acid.

The following Examples are intended to be illustrative and in no way are to be construed as limiting the invention.

EXAMPLE 1

The following reactions will illustrate the selectivity of halogenation as realized by the invention. The reaction is accomplished by simply bubbling halogen gas through an alcoholic solution of secondary alcohol or chlorohydrin. All the reactions are conducted in a 250 ml 3 necked flask at room temperature and atmospheric pressure accomplished by moderate agitation. The ratio of halogen to secondary alcohol or halohydrin is 1:1 molar basis and the ratio of solvent to reactant, i.e., halohydrin or secondary alcohol is about 5:1.

The ensuing equations will illustrate the yield and selectivity of the instant invention. In all cases the product was extracted with ether and the ether layer washed with water to remove the ethylene glycol, when used. When methanol was used as solvent, the resulting solution is either treated with water or subjected to a vacuum to remove the solvent.

Products are analyzed by NMR run in CDCl$_3$ containing 1% TMS.

To a 250 ml, 3 neck flask, equipped with a mechanical stirrer, is added 6 grams isopropanol (0.1 mole) and 100 mls methanol. Chlorine gas is bubbled in slowly. Every 10 minutes, one ml of solution is removed and analyzed by NMR. After a total of 0.3 moles of chlorine has been added the reaction is stopped. The solution is cooled to −70°C and 6 grams of $$\underset{ClCH_2}{\overset{CH_3O}{\diagdown}}\underset{CH_2Cl}{\overset{OCH_3}{\diagup}}C$$

crystallized out. NMR shows two peaks in the ratio of 4:6. The OCH$_3$ protons appear at 3.28 and the CH$_2$Cl at 3.63δ. The filtrate is rich in $$\underset{CH_3}{\overset{CH_3O}{\diagdown}}\underset{CH}{\overset{OCH_3}{\diagup}}C\underset{Cl}{\overset{Cl}{\diagdown}}$$

(11 grams collected) and its NMR showed the OCH$_3$ protons are at 3.28δ, the CH$_3$ protons at 1.52δ and the $$CH\underset{Cl}{\overset{Cl}{}}$$

protons at 5.79δ. Chlorination of this compound yields $$\underset{Cl}{\overset{CH_3O}{}}\underset{CH}{\overset{}{\diagdown}}C\underset{CH_2Cl}{\overset{OCH_3}{\diagup}}$$
$$Cl$$

The NMR spectra shows the OCH$_3$ protons at 3.47δ, the CH$_2$Cl at 4.15δ and the $$CH\underset{Cl}{\overset{Cl}{}}$$

at 6.07δ.

EXAMPLE 2

To a 250 ml, 3 neck flask equipped with a mechanical stirrer, is added 9 grams (0.1 mole) 1chloro-2-propanol and 80 mls methanol chlorinated slowly, and removed samples every 15 minutes for analyses via NMR. After 0.3 moles of Cl$_2$ has beed added, the product is cooled to -70°C and two grams of $$\underset{CH_2Cl}{\overset{CH_3O}{\diagdown}}C\underset{CH_2Cl}{\overset{OCH_3}{\diagup}}$$

(11% yield) was collected by filtration. The rest of the solution consisted mainly of unreacted 1-chloro-2-propanol.

EXAMPLE 3

A 250 ml, 3 neck flask equipped with stirrer is charged with 14 grams (.11 moles)α-methyl benzyl alcohol and 100 mls ethylene glycol. The mixture is chlorinated slowly until 0.10 mole Cl$_2$ has passed through. The solid which has precipitated out is filtered and washed with water. Eight grams (0.04 mole) of product is collected.

NMR. 1. CH$_2$Cl at 3.75δ one peak
2. Protons 1, 2, 3, 4

2 mulitplets - one at 3.79-4.00δ one at 4.00-4.25δ
The two multiplets exhibit ABCD coupling i.e. all the protons are not identical due to being in different environments
3. Phenyl protons - multiplet 7.2-7.7δ The proton ratio is 5:2:2:2.

EXAMPLE 4

According to the procedure of Example 1, 6.1 gm (0.05 mole) of phenethyl alcohol and 100 mls of ethylene glycol are charged into a 250 ml 3 necked flask. Br$_2$ is added slowly, dropwise, thereto at about room temeprature (16 gms BR$_2$ = 0.1 mole). 5 gms (41.7% yield) of was crystallized out at −70°C.

EXAMPLE 5

According to the procedure of Example 4, 10 gms (0.2moles) of isopropanol and 100 ml of methanol are charged to a 250 ml 3 necked flask. 60 gms of Br$_2$ (0.38 mole) is added, dropwise, over a period of 3 days. The solution was cooled to −70°C and 27.5 gm (51% yield) of $$(CH_3O)_2-C\underset{CH_2Br}{\overset{CH_2Br}{\diagup}}$$

was recovered.

EXAMPLE 6

According to the procedure of Example 4, 8.8 gms (0.1 mole) of methyl isopropyl carbinol along with 100 gms of ethylene glycol is placed into a 250 ml 3 necked flask. 32 gms (0.2 mole) of Br$_2$ is added dropwise over a 2 hour period. The solution is then extracted with ether and washed with water. 17.1 (81% yield) gms of

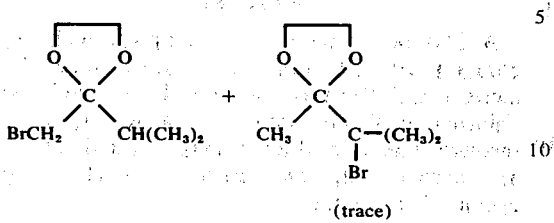

(trace)

EXAMPLE 7

According to the procedure of Example 4, 5.1 gms (0.051mole) of methyl-t-butyl carbinol and 100 ml of ethylene glycol are charged to a 250 ml 3 necked flask. 16 gm (0.1 mole) $Br_2$ is added slowly, dropwise, over a period of 2 hours. The solution is extracted with ether and washed with water. 10.5 gms of product which consisted of

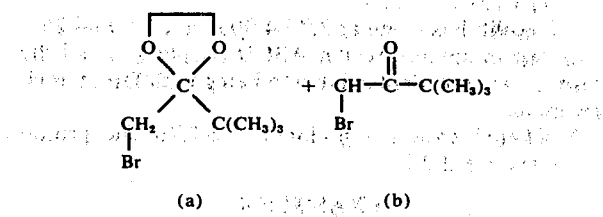

in a mole % ratio of a:b 82.6%:17.4%.

What is claimed is:

1. A method for preparing selectively halogenated ketones comprising:
   a. preparing selectively halogenated ketals, by reacting a secondary alcohol or halohydrin compound, of the general formula

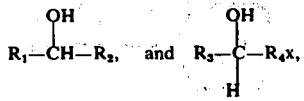

with chlorine or bromine, wherein $x$ is chlorine or bromine, in the presence of an alcohol selected from the group consisting of
   i. monohydric and polyhydric alcohols having 1 to 5 carbon atoms wherein, further, each C—H group of said monohydric and polyhydric alcohols has a hydroxyl group attached thereto,
   ii. ethanol,
   iii. 2,3 butanediol, and
   iv. propylene glycol,
   wherein the ratio of said alcohol to said secondary alcohol or halohydrin is from about 5:1 to about 20:1, wherein said reaction is carried out at a temperature of from about 0°C to about 80°C, and wherein $R_1$, $R_2$, $R_3$ and $R_4$ are independently selected from the group consisting of
   i. straight chain alkyl groups of from 1 to 20 carbon atoms,
   ii. alkylaryl groups wherein the alkyl moiety is a straight chain alkyl group of from 1 to 20 carbon atoms,
   iii. branched chain alkyl groups of from 3 to 20 carbon atoms provided that when either $R_1$ or $R_2$ of the pair $R_1$ and $R_2$, or $R_3$ or $R_4$ of the pair $R_3$ and $R_4$ is a branched chain, the other member is a straight chain alkyl group as previously defined, and
   iv. a phenyl group, provided that when either $R_1$ or $R_2$ of the pair $R_1$ and $R_2$, or $R_3$ or $R_4$ of the pair $R_3$ and $R_4$ is phenyl, the other member is a straight chain alkyl group as previously defined, or wherein $R_1$ and $R_2$ or $R_3$ and $R_4$ may be taken together to form a cyclo alkyl ring having at least six carbon atoms in said ring; and
   b. subsequently hydrolyzing said selectively halogenated ketals under acid conditions.

2. A method according to claim 1 wherein the secondary alcohol is selected from the group consisting of isopropanol, 2-pentanol, 3-hexanol, sec-2-phenethyl alcohol, 1-phenyl-2-propanol, cyclohexanol, cyclooctanol, 3-methyl-2-butanol, 4,4-dimethyl-2-pentanol, methyl-t-butyl carbinol.

3. A method according to claim 1 wherein the halohydrin is selected from the group consisting of chlorohydrin, bromohydrin, 3-chloro-2-pentanol, 3-bromo-2-heptanol, 1-phenyl-3-bromo-2-propanol, 4,4-dimethyl-3-chloro-2-pentanol, 3,3dimethyl-1-bromo-2-butanol.

4. A method according to claim 1 wherein the ratio of alcohol to secondary alcohol or halohydrin is about 5:1 to about 10:1.

5. A method according to claim 1 wherein the molar ratio of said halogen to said secondary alcohol or halohydrin is from about 2:1 to about 5:1.

6. A method for preparing selectively and symmetrically dihalogenated ketones comprising:
   a. preparing selectively and symmetrical dihalogenated ketals, by reacting secondary alcohol or halohydrin compound, of the general formula

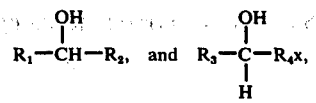

with chlorine or bromine, wherein $x$ is chlorine or bromine, in the presence of an alcohol selected from the group consisting of
   i. monohydric and polyhydric alcohols having 1 to 5 carbon atoms wherein, further, each C—H group of said monohydric and polyhydric alcohols has a hydroxyl group attached thereto,
   ii. ethanol,
   iii. 2,3 butanediol, and
   iv. propylene glycol,
   wherein the ratio of said alcohol to said secondary alcohol or halohydrin is from about 5:1 to about 20:1, wherein said reaction is carried out at a temperature of from about 0°C to about 80°C, and wherein $R_1$, $R_2$, $R_3$ and $R_4$ are independently selected from the group consisting of
   i. straight chain alkyl groups of from 1 to 20 carbon atoms,
   ii. alkylaryl groups wherein the alkyl moiety is a straight chain alkyl group of from 1 to 20 carbon atoms, and
   iii. branched chain alkyl groups of from 3 to 20 carbon atoms provided that when either $R_1$ or $R_2$ of the pair $R_1$ and $R_2$, or $R_3$ or $R_4$ of the pair $R_3$ and R₄ is a branched chain, the other member is a straight chain alkyl group as previously defined, or wherein R₁ and R₂ ro R₃ and R₄ may be taken together to form a cyclo alkyl ring having at least six carbon atoms in said ring; and b. subsequently hydrolyzing said selectively and symmetrically dihalogenated ketals under acid conditions.

7. A method according to claim 6 wherein the secondary alcohol is selected from the group consisting of isopropanol, 2-pentanol, 3-hexanol, sec-2-phenethyl alcohol, 1-phenyl-2-propanol, cyclohexanol, cyclooctanol, 3-methyl-2-butanol, 4,4-dimethyl-2-pentanol, methyl-t-butyl carbinol.

8. A method according to claim 6 wherein the halohydrin is selected from the group consisting of chlorohydrin, bromohydrin, 3-chloro-2-pentanol, 3-bromo-2-heptanol, 1-phenyl-3-bromo-2-propanol, 4,4-dimethyl-3-chloro-2-pentanol, 3,3-dimethyl-1-bromo-2-butanol.

9. A method according to claim 6 wherein the ratio of alcohol to secondary alcohol or halohydrin is about 5:1 to about 10:1.

10. A method according to claim 6 wherein the molar ratio of said halogen to said secondary alcohol or halohydrin is from about 2:1 to about 5:1.

11. A method for preparing symmetrically chlorinated ketones comprising:

a. preparing symmetrically chlorinated ketals, by reacting in methanol, secondary alcohol or chlorohydrin compounds, of the general formula

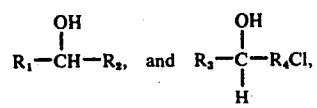

with gaseous chlorine, wherein the ratio of said methanol to said secondary alcohol or halohydrin is from about 5:1 to about 20:1, wherein said reaction is carried out at a temperature of about 25°C, and wherein $R_1$, $R_2$, $R_3$ and $R_4$ are independently selected from the group consisting of i. straight chain alkyl groups of from 1 to 20 carbon atoms, and ii. alkylaryl groups wherein the alkyl moiety is a straight chain alkyl group of from 1 to 20 carbon atoms, or wherein $R_1$ and $R_2$ or $R_3$ and $R_4$ may be taken together to form a cyclo alkyl ring having at least six carbon atoms in said ring; and b. subsequently hydrolyzing said symmetrically dichlorinated ketals under acid conditions.

* * * * *

UNITED STATES PATENT AND TRADEMARK OFFICE
CERTIFICATE OF CORRECTION

PATENT NO. : 3,985,808
DATED : October 12, 1976
INVENTOR(S) : Eddie N. Gutierrez et al It is certified that error appears in the above-identified patent and that said Letters Patent are hereby corrected as shown below:

Col. 9, lines 37, 38 change "CH$\begin{smallmatrix}Cl\\Cl\end{smallmatrix}$" to -- CH$\begin{smallmatrix}\diagup Cl\\ \diagdown Cl\end{smallmatrix}$ --.

Col. 9, lines 51, 52 change "CH$\begin{smallmatrix}Cl\\Cl\end{smallmatrix}$" to -- CH$<\begin{smallmatrix}Cl\\Cl\end{smallmatrix}$ --.

Col. 10, line 24 change "3.75δone" to --3.75δ one--.

Col. 2, line 27 change "1 20" to --1 to 20--.

Col. 7, line 61 change "alchohol" to --alcohol--.

Col. 10, line 26 change "3.79-4.00δone" to --3.79-4.00δ one--.

Col. 10, lines 37, 38 change "temeprature" to --temperature--.

Col. 10, line 38 "BR$_2$" should be --Br$_2$--.

Signed and Sealed this

Eighth Day of February 1977

[SEAL]

Attest:

RUTH C. MASON
Attesting Officer

C. MARSHALL DANN
Commissioner of Patents and Trademarks